United States Patent [19]

Kanzler et al.

[11] Patent Number: 4,971,047

[45] Date of Patent: Nov. 20, 1990

[54] TREATING BURNS

[76] Inventors: Graham L. B. Kanzler, 22 Wellington Street; Mary M. Salmon-Lomas, 28 Ulster Road, both of Albany, Western Australia, Australia

[21] Appl. No.: 271,952

[22] PCT Filed: Aug. 21, 1987

[86] PCT No.: PCT/AU87/00283
§ 371 Date: Aug. 19, 1988
§ 102(e) Date: Aug. 19, 1988

[87] PCT Pub. No.: WO88/01157
PCT Pub. Date: Feb. 25, 1988

[30] Foreign Application Priority Data

Aug. 21, 1986 [AU] Australia .............................. PH7573

[51] Int. Cl.⁵ .............................................. A61F 13/00
[52] U.S. Cl. ............................. 128/157; 128/DIG. 24; 128/165; 128/870
[58] Field of Search .................. 128/157, 165, 204.26, 128/205.26, 869, 870, 872, 874, 878, 879; 2/16, 21, 22; 5/82, 89

[56] References Cited

U.S. PATENT DOCUMENTS

| 1,554,692 | 9/1925 | Shane | 128/849 |
| 2,461,872 | 2/1949 | Beatty | 2/21 |
| 2,766,751 | 10/1956 | Topa | 128/873 |
| 3,601,824 | 8/1971 | Bradford | 5/82 |
| 3,824,998 | 7/1974 | Snyder | 128/856 |
| 3,986,505 | 10/1976 | Power | 128/846 |
| 4,579,753 | 4/1986 | Gjendemsjo | 5/82 R |

Primary Examiner—Robert A. Hafer
Assistant Examiner—Kevin G. Rooney
Attorney, Agent, or Firm—Harness, Dickey & Pierce

[57] ABSTRACT

Apparatus for providing emergency treatment to a burns patient. The apparatus includes a bag (11) having a wall (15) which defines a space (16) for receiving the burns patient so as to provide a protective environment about the patient. The bag (11) comprises a first portion (21) constructed of flexible waterproof material and a second portion (22) constructed of fluid permeable material. The second portion is so arranged as to be upwardly facing when the bag is in use and is detachable from the first portion to provide access to the space within the bag.

9 Claims, 2 Drawing Sheets

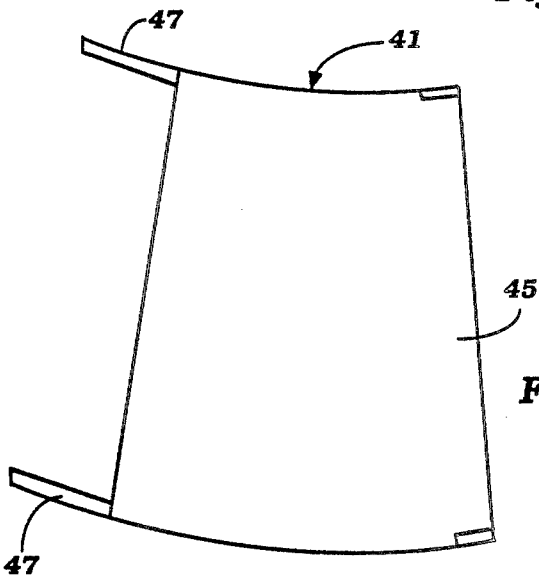
Figure 2
Figure 3
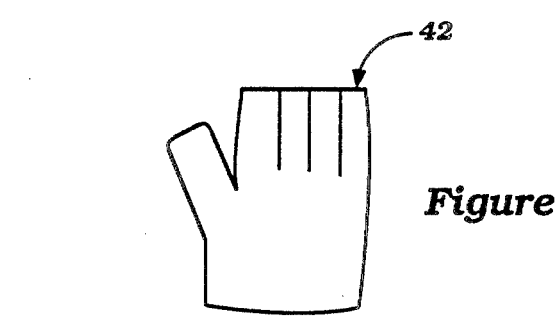
Figure 4
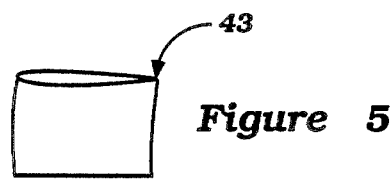
Figure 5

TREATING BURNS

This invention relates to an apparatus for treating burns and other wounds upon human beings.

In providing emergency treatment to a burns patient, it is desirable to provide a protective (preferably sterile) environment around the wounded portion of the patient while he or she is transported from the accident scene to a hospital or other location at which proper medical treatment can be provided.

The present invention seeks to provide an apparatus for treating burns and other wounds which can provide a protective environment into which a burns patient may be placed while he or she is transported to another location for further treatment.

In one form the invention resides in an apparatus for treating burns and other wounds comprising a bag having a wall defining a space to receive at least part of the body of a burns patient, the bag including a fluid permeable portion so arranged as to be upwardly facing when the bag is in use.

With this arrangement, liquid (such as a saline solution which may provide relief to the patient) can be introduced into the space within the bag through the fluid permeable portion.

Preferably, the wall of the bag includes a first portion of a construction impervious to liquid and a second portion which is at last partially detachable from the first portion to provide access to the space within the bag, said second portion comprising said fluid permeable portion.

Preferably, the bag is constructed to receive the torso, and limbs of the burns patient, said second portion being elongated and permanently secured at one end thereof to the first portion, and fastening means being provided to releasably attach the two longitudinal sides of the second portion to the first portion.

Preferably, said fastening means also releasably attaches the other end of the second portion to the first portion of the bag.

The invention will be better understood by reference to the following description of one specific embodiment thereof as shown in the accompanying drawings in which:

FIG. 2 is a cross sectional view along the line 2—2 of FIG. 1;

FIG. 3 is a schematic view of a first accessory device for use with the embodiment;

FIG. 4 is a schematic view of a second accessory device for use With the embodiment;

FIG. 5 is a schematic view of a third accessory device for use with the embodiment.

Figure 1:
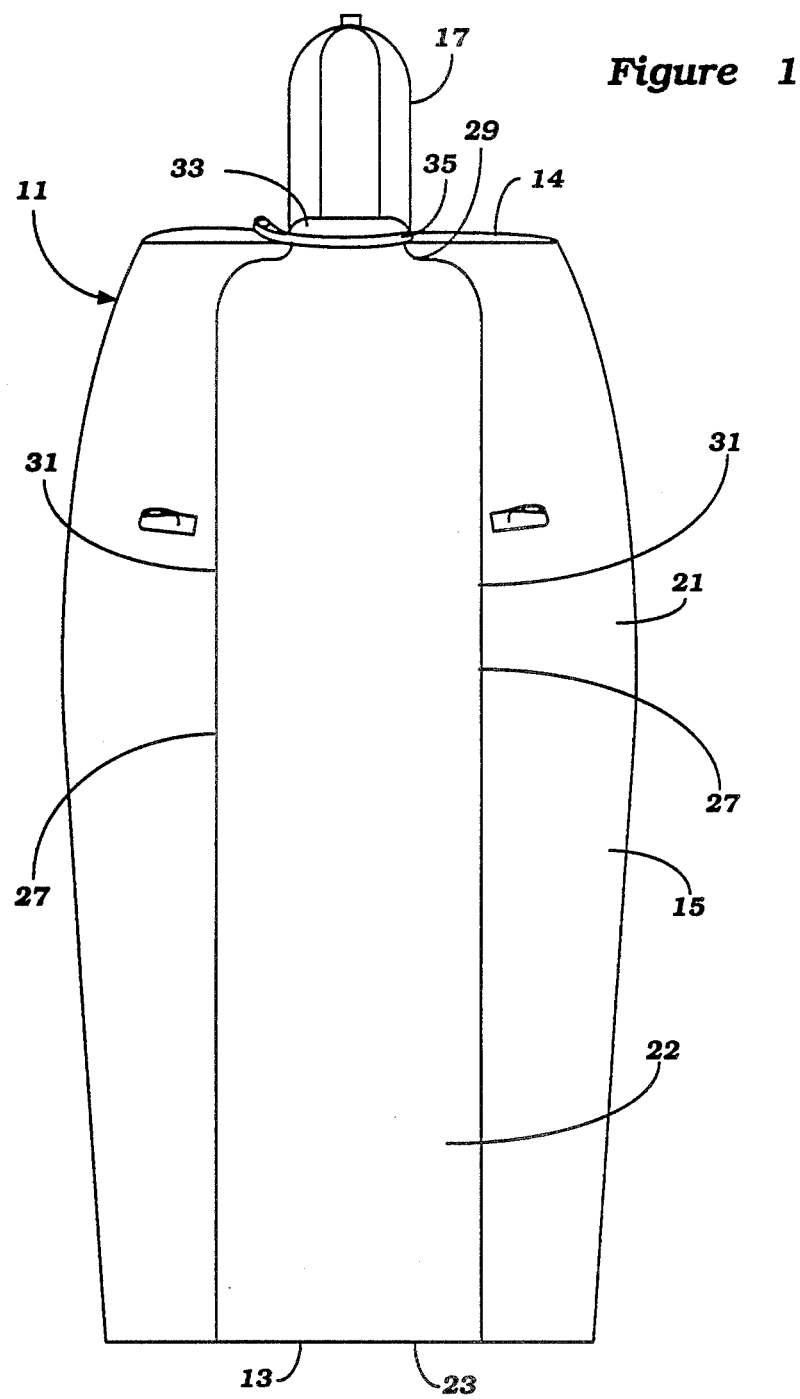
FIG. 1 is a schematic plan view of a treatment apparatus according to the embodiment.

The embodiment shown in the drawings is directed to apparatus for providing emergency treatment to a burns patient at the scene of the accident. The device enables the burns patient to be maintained in a protective environment which is substantially sterile while being transported to a hospital or other location for proper medical treatment.

The apparatus comprises a bag 11 having a foot end 13 and a head end 14. The bag has a wall 15 defining a space 16 which is arranged to receive the torso and limbs of the burns patient with the head of the burns patient projecting beyond the head end 14. A hood 17 is attached to the bag for receiving the head of the burns patient.

The wall 15 of the bag 11 comprises a first portion 21 and a second portion 22. The second portion 22 is so arranged as to be upwardly facing when the bag is in use; that is, when a patient is in a supine position within the bag.

The first portion 21 of the bag Wall is formed of a flexible waterproof material lined internally with a material such as Melolin, which can hold fluid in suspension and which does not adhere to wounds upon the body of the patient.

The second portion 22 of the bag wall is made of fluid permeable material such as Melolin.

The second portion 22 is partially detachable from the first portion to provide access to the space 16 within the bag. More particularly, the second portion 22 extends along substantially the full length of the bag and is permanently secured at one end 23 thereof to the first portion 21 at or near the foot end 13 of the bag. A fastening means 25 is provided to releasably attach the two longitudinal sides 27 and the other end 29 of the second portion 22 to the first portion 21. The fastening means includes a zipper fastener 31 extending along each longitudinal side 27 of the second portion and a protective tongue 33 at said other end 29 of the second portion releasably engagable with a fastening strap 35 at the head end 14 of the bag.

Carrying straps (not shown) are provided on each side of the bag 11 to provide a convenient means of carrying the burns patient within the bag. The carrying straps can be aligned along each side of the bag and be adapted if desired to receive carrying poles to provide for carrying the bag like a litter.

The bag 11 is stored ready for use with the first portion 21 and hood 17 maintained in a sterile condition within a sealed package (not shown) such as a plastic bag and the second portion 22 mentioned in a sterile condition within a further sealed package (not shown).

In addition to the bag 11 and hood 17, the burns treatment apparatus may include several accessory devices including at least one limb wrap 41, at least one glove 42 and at least one pad 43, each of Which is stored ready for use in a sterile condition within a sealed package. The limb wrap 41 is of a construction illustrated in FIG. 3 of the drawings and includes a portion 45 which is adapted to be wrapped around an injured limb of the burns patient and held in such a position by releasable fastening means 47 such as "Velcro" fasteners. The inner surface at least of the portion 45 of the limb wrap 41 is provided by material, such as Melolin, which can hold liquid and which does not adhere to burns upon the patient's limbs. The glove 42 is illustrated in FIG. 4 of the drawings and is arranged to treat any burns on a hand of a burns patient and to separate the fingers from each other. The glove is lined internally at least with material which can hold liquid and which does not adhere to burns upon the patient. The pad, 43 is illustrated in FIG. 5 and intended to be positioned in an armpit or groin region of a burns patient if such region requires treatment. The pad has a surface lining which can hold liquid and which does not adhere to burns upon the patient.

The bag 11 and other components of the burns treatment apparatus can form part of a kit which also includes a supply of saline solution (or other liquid) which can be applied to the burns patient for the purpose of cooling or otherwise treating the burns.

The burns treatment kit can be carried by emergency services personnel such as fire-fighting, police and ambulance teams, and paramedics in industrial and military situations. The kit enables a burns patient to be treated at the scene of the accident and then transported to a hospital for proper treatment.

Emergency treatment of a burns patient using the kit will now be described. When a burns patient requires emergency treatment, protective package for the first portion 21 and hood 17 of the bag 11 is removed. The second portion 22 of the bag is positioned at the foot end of the bag so that the burns patient can be placed in a supine position in the bag. Before the patient is so placed in the bag, the internal lining within the first portion 21 of the bag and the internal lining within the hood 17 are saturated with the saline solution supplied With the kit. The burns patient is then placed in a supine position within the first portion of the bar without removing the patient's clothing. The hood 17 is fitted around the head of the patent and any required accessories, such as limb wraps, gloves or pads, are located on the body of the patient (after first having been saturated with saline solution).

The protective package for the second portion 22 of the bag 11 is then removed and the bag closed by fastening the second portion in position in the manner described previously. In this way, the bag provides a sterile protective environment about the body of the burns patient and a convenient means of transporting the patient to hospital for further treatment.

Once the bag has been closed about the burns patient, any additional saline solution which may be required can be introduced into the bag through the fluid permeable second portion 22 simply by pouring the solution onto that portion of the bag.

The fluid permeable second portion 22 of the bag is upwardly facing and saline solution within the bag is maintained within the confines of the first portion which is waterproof.

If the skin temperature of the patient falls or if the combined weight of the patient and treatment apparatus is required to be reduced so that the patient can be carried. some liquid can be removed from the bag by detaching one longitudinal side of the second portion, from the remainder of the bag and then laying that side flat to permit liquid to drain from the bag.

If the patient requires blood transfusions or intravenous feeding when in the bag, access to the patient can be gained by detaching one longitudinal of the second portion 22 of the bag from the first portion thereof.

In addition to treating a burns patient in the manner described above, apparatus according to the invention may be used to treat a patient with burns or other wounds without using a saline solution or other liquid to provide a moist environment within the bag and may be used after the application of creams or other treatments to the wound. The apparatus may, for example, be used simply to provide a protective (but not necessarily sterile) environment about an injured person while that person is transported from the scene of an accident.

The claims defining the invention are as follows; we claim:

1. Apparatus for treating burns and other wounds comprising a bag having a wall defining a space to receive at least part of the body of a patient, the wall including a first portion of a construction impervious to liquid for containing liquid introduced into the bag and a second fluid permeable portion which is at least partially detachable from the first portion to provide access to the space within the bag and is so arranged as to be upwardly facing when the bag is in use.

2. Apparatus according to claim 1 or 2 wherein the bag is constructed to receive the torso and limbs of the patient, said second portion being elongated and permanently secured at one end thereof to the first portion, and fastening means being provided to releasably attach the two longitudinal sides of the second portion to the first portion.

3. Apparatus according to claim 3 wherein said fastening means also releasably attaches the other end of the second portion to the first portion of the bag.

4. Apparatus according to claim 1 wherein said first portion is constructed of flexible waterproof material lined internally with material which can hold liquid in suspension and which does not adhere to wounds upon the body of the patient.

5. Apparatus according to claim 1 wherein said second fluid permeable portion is constructed of material which can hold fluid in suspension and which does not adhere to wounds upon the body of the patient.

6. Apparatus according to claim 2 further comprising a hood at said other end of the bag for receiving the head of a patient.

7. A kit of parts including a bag according to claim 2 and further including a limb wrap having a lining which can hold liquid in suspension and which does not adhere to wounds on a limb of a patient.

8. A kit of parts including a bag according to claim 2 and further including a protective glove which can hold liquid in suspension and which does not adhere to wounds on a hand of a patient.

9. A kit of parts including a bag according to claim 2 and further including a pad having a covering which can hold liquid in suspension and which does not adhere to wounds upon the body of a patient.

* * * * *

UNITED STATES PATENT AND TRADEMARK OFFICE
CERTIFICATE OF CORRECTION

PATENT NO. : 4,971,047

DATED : November 20, 1990

INVENTOR(S) : Kanzler, et al

It is certified that error appears in the above-identified patent and that said Letters Patent is hereby corrected as shown below:

On the title page and Col. 1, line 1, "TREATING BURNS" should be --APPARATUS FOR TREATING BURNS--.

Column 4, line 19, Claim 2, delete "or 2".

Column 4, line 26, Claim 3, "3" (second occurrence) should be --2--.

Signed and Sealed this

Twenty-second Day of December, 1992

Attest:

DOUGLAS B. COMER

Attesting Officer

Acting Commissioner of Patents and Trademarks